(12) United States Patent
Stedman et al.

(10) Patent No.: US 11,426,536 B2
(45) Date of Patent: *Aug. 30, 2022

(54) LIQUID DRUG CARTRIDGES AND ASSOCIATED DISPENSER

(71) Applicant: Aerami Therapeutics, Inc., Durham, NC (US)

(72) Inventors: Benjamin Stedman, Brisbane, CA (US); Jim Fink, Brisbane, CA (US); Lisa Molloy, Brisbane, CA (US); Matt Sander, Brisbane, CA (US)

(73) Assignee: AERAMI THERAPEUTICS, INC., Durham, NC (US)

( * ) Notice: Subject to any disclaimer, the term of this patent is extended or adjusted under 35 U.S.C. 154(b) by 555 days.

This patent is subject to a terminal disclaimer.

(21) Appl. No.: 16/397,756

(22) Filed: Apr. 29, 2019

(65) Prior Publication Data

US 2019/0321568 A1 Oct. 24, 2019

Related U.S. Application Data

(63) Continuation of application No. 14/732,446, filed on Jun. 5, 2015, now Pat. No. 10,307,550.

(Continued)

(51) Int. Cl.
*A61M 11/00* (2006.01)
*A61M 15/00* (2006.01)
*A61M 5/31* (2006.01)

(52) U.S. Cl.
CPC ......... *A61M 11/007* (2014.02); *A61M 11/005* (2013.01); *A61M 11/006* (2014.02);
(Continued)

(58) Field of Classification Search
CPC ... A61B 5/082; A61B 5/14539; A61B 5/1477; A61J 7/0418; A61M 11/00;
(Continued)

(56) References Cited

U.S. PATENT DOCUMENTS 3,736,932 A 6/1973 Satchell
3,789,843 A 2/1974 Armstrong et al.
(Continued)

FOREIGN PATENT DOCUMENTS

CN 1198689 11/1998
CN 1246017 3/2000
(Continued)

OTHER PUBLICATIONS

European Application No. EP15806240.6 received an Office Action dated Jul. 17, 2020, 5 pages.
(Continued)

*Primary Examiner* — Annette Dixon
(74) *Attorney, Agent, or Firm* — Kilpatrick Townsend & Stockton LLP

(57) ABSTRACT

Liquid drug cartridges and an associated inhaler are used to deliver one more separate doses of an aerosolized liquid drug. A cartridge includes a container for storing the liquid drug, an end cap having an ejection opening, a filter element, and a piston that is repositionable relative to the container to selectively eject a volume of liquid drug from the ejection opening. The filter element filters the liquid drug prior to ejection from the ejection opening. The liquid drug cartridge can be coupled with an inhaler that includes an aerosol generator. The aerosol generator includes a vibratable membrane onto which the liquid drug is ejected. The liquid drug is aerosolized by the vibration of the membrane for inhalation by a user.

20 Claims, 9 Drawing Sheets

Related U.S. Application Data

(60) Provisional application No. 62/099,806, filed on Jan. 5, 2015, provisional application No. 62/009,704, filed on Jun. 9, 2014.

(52) U.S. Cl.
CPC ........ *A61M 15/002* (2014.02); *A61M 15/009* (2013.01); *A61M 15/0033* (2014.02); *A61M 15/0035* (2014.02); *A61M 15/0036* (2014.02); *A61M 15/0085* (2013.01); *A61M 15/0086* (2013.01); *A61M 5/3145* (2013.01); *A61M 11/003* (2014.02); *A61M 15/001* (2014.02); *A61M 15/0066* (2014.02); *A61M 15/0091* (2013.01); *A61M 2205/75* (2013.01)

(58) Field of Classification Search
CPC .......... A61M 11/001; A61M 11/002; A61M 11/003; A61M 11/005; A61M 11/006; A61M 11/007; A61M 15/00; A61M 15/001; A61M 15/002; A61M 15/0021; A61M 15/0028; A61M 15/0033; A61M 15/0035; A61M 15/0036; A61M 15/0065; A61M 15/0066; A61M 15/008; A61M 15/0085; A61M 15/0086; A61M 15/009; A61M 15/0091; A61M 15/0096; A61M 15/025; A61M 16/0858; A61M 16/202; A61M 2016/0021; A61M 2016/0027; A61M 2016/0036; A61M 2016/0039; A61M 2202/064; A61M 2205/0233; A61M 2205/053; A61M 2205/057; A61M 2205/073; A61M 2205/3303; A61M 2205/3306; A61M 2205/50; A61M 2205/502; A61M 2205/52; A61M 2205/60; A61M 2205/6018; A61M 2205/6027; A61M 2205/6036; A61M 2205/6045; A61M 2205/75; A61M 2205/8206; A61M 2205/8212; A61M 2209/10; A61M 2230/43; A61M 5/3145; B01F 15/0201; B01F 15/0254; B01F 3/04049; B05B 11/00416; B05B 11/0059; B05B 11/309; B05B 11/3094; B05B 12/08; B05B 17/0646; B05B 17/0676; B05B 17/0684; B41J 2/025; B82Y 15/00; C25D 1/08; F16H 35/00; G01F 1/363; G01F 1/40; G01F 1/44; G01F 1/50; G01F 13/006; G01F 15/002; G01F 25/0007; G01F 7/005; G01N 1/22; G01N 2001/2244; G01N 2800/12; G01N 33/54313; G01N 33/569; G01N 33/6893

See application file for complete search history.

(56) References Cited

U.S. PATENT DOCUMENTS

| | | | |
|---|---|---|---|
| 3,938,513 A | 2/1976 | Hargest | |
| 4,218,541 A | 8/1980 | Ackerman | |
| 4,331,146 A | 5/1982 | Brignola | |
| 4,424,057 A | 1/1984 | House | |
| 4,453,927 A | 6/1984 | Sinko | |
| 5,060,642 A | 10/1991 | Gilman | |
| 5,164,740 A | 11/1992 | Ivri | |
| 5,333,106 A | 7/1994 | Lanpher et al. | |
| 5,347,998 A | 9/1994 | Hodson et al. | |
| 5,354,287 A | 10/1994 | Wacks | |
| 5,363,842 A | 11/1994 | Mishelevich et al. | |
| 5,364,838 A | 11/1994 | Rubsamen | |
| 5,404,871 A * | 4/1995 | Goodman | A61M 15/00 |
| | | | 128/200.14 |
| 5,435,282 A * | 7/1995 | Haber | A61M 15/0065 |
| | | | 128/200.14 |
| 5,479,920 A | 1/1996 | Piper et al. | |
| 5,515,842 A | 5/1996 | Ramseyer | |
| 5,586,550 A | 12/1996 | Ivri et al. | |
| 5,617,845 A * | 4/1997 | Poss | A61M 15/0096 |
| | | | 128/203.15 |
| 5,672,581 A | 9/1997 | Rubsamen et al. | |
| 5,743,250 A | 4/1998 | Gonda et al. | |
| 5,758,637 A | 6/1998 | Ivri et al. | |
| 5,759,101 A | 6/1998 | Kohorn | |
| 5,884,620 A | 3/1999 | Gonda et al. | |
| 5,915,378 A | 6/1999 | Lloyd et al. | |
| 5,938,117 A | 8/1999 | Ivri | |
| 5,941,240 A | 8/1999 | Gonda et al. | |
| 5,950,619 A | 9/1999 | van der Linden | |
| 5,970,974 A | 10/1999 | Van der Linden | |
| 6,014,970 A | 1/2000 | Ivri et al. | |
| 6,062,212 A | 5/2000 | Davison et al. | |
| 6,085,740 A | 7/2000 | Ivri et al. | |
| 6,085,753 A | 7/2000 | Gonda et al. | |
| 6,089,260 A | 7/2000 | Jaworski et al. | |
| 6,098,615 A | 8/2000 | Lloyd et al. | |
| 6,205,999 B1 * | 3/2001 | Ivri | A61M 15/0028 |
| | | | 128/200.22 |
| 6,267,154 B1 | 7/2001 | Felicelli et al. | |
| 6,408,854 B1 | 6/2002 | Gonda et al. | |
| 6,427,682 B1 | 8/2002 | Klimowicz et al. | |
| 6,467,476 B1 | 10/2002 | Ivri et al. | |
| 6,540,153 B1 | 4/2003 | Ivri | |
| 6,540,154 B1 | 4/2003 | Ivri et al. | |
| 6,629,646 B1 | 10/2003 | Ivri | |
| 6,640,804 B2 | 11/2003 | Ivri et al. | |
| 6,647,987 B2 | 11/2003 | Gonda et al. | |
| 6,688,304 B2 | 2/2004 | Gonda et al. | |
| 6,755,189 B2 | 6/2004 | Ivri et al. | |
| 6,814,071 B2 | 11/2004 | Klimowicz et al. | |
| 6,890,517 B2 | 5/2005 | Drechsel | |
| 6,921,020 B2 | 7/2005 | Ivri | |
| 6,926,208 B2 | 8/2005 | Ivri | |
| 6,978,941 B2 | 12/2005 | Litherland et al. | |
| 7,028,686 B2 | 4/2006 | Gonda et al. | |
| 7,032,590 B2 | 4/2006 | Loeffler et al. | |
| 7,040,549 B2 | 5/2006 | Ivri et al. | |
| 7,066,398 B2 | 6/2006 | Borland et al. | |
| 7,083,112 B2 | 8/2006 | Ivri | |
| 7,100,600 B2 | 9/2006 | Loeffler et al. | |
| 7,108,197 B2 | 9/2006 | Ivri | |
| 7,174,888 B2 | 2/2007 | Ivri et al. | |
| 7,195,011 B2 | 3/2007 | Loeffler et al. | |
| 7,219,664 B2 | 5/2007 | Ruckdeschel et al. | |
| 7,448,375 B2 | 11/2008 | Gonda et al. | |
| 7,451,760 B2 | 11/2008 | Denyer et al. | |
| 7,544,189 B2 | 6/2009 | Griffiths | |
| 7,600,512 B2 | 10/2009 | Lee et al. | |
| 7,628,339 B2 | 12/2009 | Ivri et al. | |
| 7,683,029 B2 | 3/2010 | Hindle et al. | |
| 7,721,730 B2 | 5/2010 | Hamano et al. | |
| 7,819,115 B2 | 10/2010 | Sexton et al. | |
| 8,082,918 B2 | 12/2011 | Jansen et al. | |
| 8,950,394 B2 | 2/2015 | Patton et al. | |
| 9,004,061 B2 | 4/2015 | Patton et al. | |
| 10,307,550 B2 * | 6/2019 | Stedman | A61M 11/005 |
| 10,610,651 B2 | 4/2020 | Stedman | |
| 2002/0011247 A1 | 1/2002 | Ivri et al. | |
| 2002/0111063 A1 | 8/2002 | Kerr | |
| 2002/0185125 A1 | 12/2002 | Klimowicz et al. | |
| 2003/0019493 A1 * | 1/2003 | Narayan | A61M 15/0085 |
| | | | 128/200.23 |
| 2003/0181478 A1 | 3/2003 | Orechsel et al. | |
| 2003/0150446 A1 | 8/2003 | Patel | |
| 2003/0192540 A1 | 10/2003 | Myman et al. | |
| 2004/0111063 A1 | 6/2004 | Botich et al. | |
| 2004/0172005 A1 | 9/2004 | Arenberg | |
| 2008/0211381 A1 | 9/2008 | Lin et al. | |
| 2009/0060977 A1 | 3/2009 | Lamson | |
| 2009/0194099 A1 | 8/2009 | Kladders | |
| 2010/0154794 A1 | 6/2010 | Valentin | |
| 2010/0274126 A1 | 6/2010 | Kobayashi et al. | |

(56) References Cited

U.S. PATENT DOCUMENTS

| | | |
|---|---|---|
| 2010/0218760 A1 | 9/2010 | Anderson et al. |
| 2010/0154793 A1 | 10/2010 | Wagner et al. |
| 2010/0319686 A1 | 12/2010 | Schennum |
| 2011/0011247 A1 | 1/2011 | Kodama et al. |
| 2011/0021999 A1 | 1/2011 | Kowalski, III et al. |
| 2011/0034878 A1 | 2/2011 | Radmer et al. |
| 2011/0114089 A1 | 5/2011 | Andersen et al. |
| 2011/0168170 A1 | 7/2011 | Patton et al. |
| 2011/0168172 A1 | 7/2011 | Patton et al. |
| 2012/0004638 A1 | 1/2012 | Zimmerman et al. |
| 2012/0041381 A1 | 2/2012 | Raj et al. |
| 2012/0183949 A1* | 7/2012 | Hyde .................. A61M 11/001 435/5 |
| 2012/0325204 A1 | 12/2012 | Holakovsky |
| 2013/0269684 A1 | 10/2013 | Patton |
| 2013/0269694 A1 | 10/2013 | Patton et al. |
| 2014/0041653 A1 | 2/2014 | Patton et al. |
| 2014/0083517 A1 | 3/2014 | Moia et al. |
| 2014/0318533 A1 | 10/2014 | Patton |
| 2015/0048119 A1 | 2/2015 | Boehm et al. |
| 2015/0352297 A1 | 12/2015 | Stedman |
| 2015/0352301 A1 | 12/2015 | Stedman |

FOREIGN PATENT DOCUMENTS

| | | |
|---|---|---|
| CN | 1454102 A | 11/2003 |
| CN | 2611051 Y | 4/2004 |
| CN | 101360524 A | 2/2009 |
| CN | 101495168 | 7/2009 |
| CN | 101720240 A | 2/2010 |
| CN | 102630173 A | 8/2012 |
| CN | 103501847 A | 1/2014 |
| RU | 2333014 C2 | 9/2008 |
| WO | 01/00261 A1 | 4/2001 |
| WO | 03/008022 A1 | 1/2003 |
| WO | 2004/028608 A1 | 4/2004 |
| WO | 2006/062449 A1 | 6/2006 |
| WO | 2008137405 A1 | 4/2008 |
| WO | 2013112579 A1 | 8/2013 |
| WO | 2013/154235 A1 | 10/2013 |
| WO | 2014035647 A1 | 3/2014 |

OTHER PUBLICATIONS

Chinese Application No. CN201580042529.2 received an Office Action dated Oct. 10, 2020, 1 pages.
BR112016028775-4 received an Office Action dated Apr. 28, 2020, 7 pages.
BR112016028840-8 received an Office Action dated Apr. 22, 2020, 7 pages.
CN201580042512.7 received a Notice of Decision to Grant dated Apr. 8, 2020 7 pages.
U.S. Appl. No. 14/732,247 received a Non-Final Office Action dated May 14, 2019. 25 pages.
U.S. Appl. No. 14/732,446 received a Corrected Notice of Allowability dated Apr. 3, 2019, 2 pages.
U.S. Appl. No. 147/32,446 received a Corrected Notice of Allowability dated Mar. 12, 2019, 2 pages.
U.S. Appl. No. 14/732,446 received a Notice of Allowance dated Jan. 17, 2019, 5 pages.
U.S. Appl. No. 147/32,446 received a Final Office Action dated Jan. 4, 3028, 27 pages.
U.S. Appl. No. 14/732,446 received a Final Office Action dated Oct. 16, 2018, 11 pages.
U.S. Appl. No. 147/32,446 received a Non-Final Office Acton dated Apr. 13, 2017, 29 pages.
U.S. Appl. No. 14/732,446 received a Non-Final Office Action dated May 8, 2018, 12 pages.
Brazilian Application No. BR112016028775-4 received an Office action dated Oct. 5, 2021, 2 pages.
European Application No. EP15806240.6 received a Notice of Decision to Grant dated Sep. 2, 2021, 1 page.
U.S. Appl. No. 16/804,677 received a Non-Final Office Action dated Sep. 22, 2021, 13 pages.

* cited by examiner

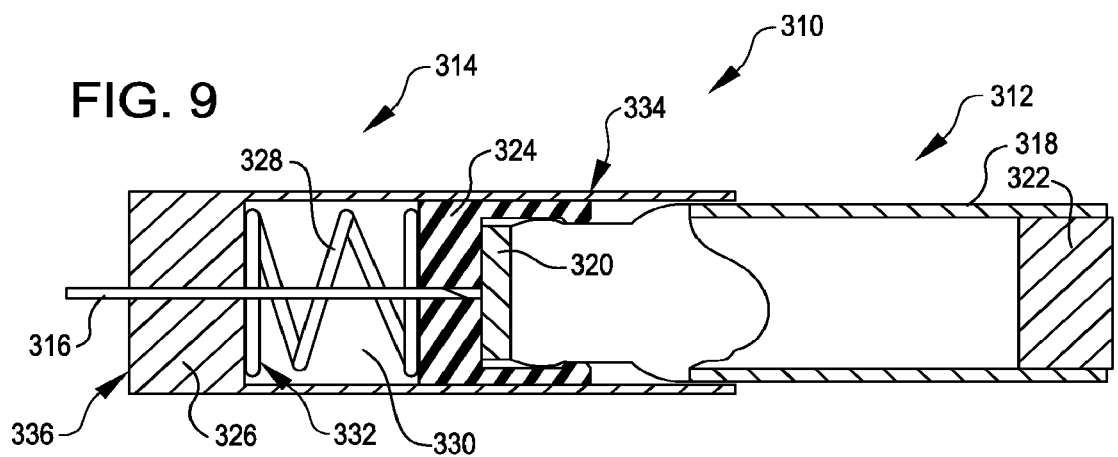
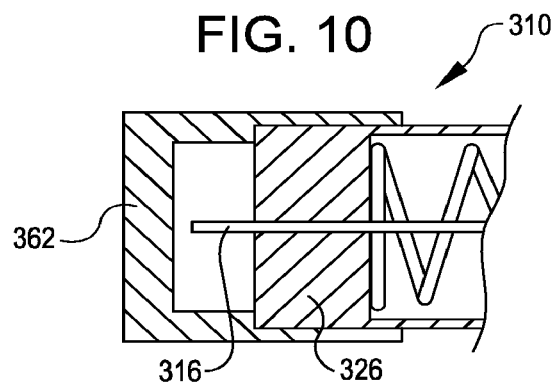

LIQUID DRUG CARTRIDGES AND ASSOCIATED DISPENSER

CROSS-REFERENCES TO RELATED APPLICATIONS

This application is a continuation of U.S. Nonprovisional application Ser. No. 14/732,446, filed Jun. 5, 2015, which claims the benefit of U.S. Provisional Application No. 62/009,704, filed Jun. 9, 2014, and claims the benefit of U.S. Provisional Application No. 62/099,806, filed Jan. 5, 2015, the contents of which are incorporated herein by reference in their entirety for all purposes.

BACKGROUND

Various types of inhalers exist for aerosolizing liquids. For example, U.S. Pat. No. 5,586,550, incorporated herein by reference, describes an inhaler that includes a dispensing apparatus in which a membrane with tapered apertures is vibrated such that liquid in contact with a rear face of the membrane is dispensed from a front face of the membrane as an aerosol.

While effective at nebulizing liquids, such inhalers may not be particularly suited for certain applications, such as aerosolizing unit doses of insulin for pulmonary delivery. Additionally, such inhalers may employ less than optimal methods with respect to liquid delivery to the dispensing apparatus, dose control, and microbial control.

Hence, improved approaches with respect to aerosolizing doses of insulin for pulmonary delivery, liquid drug delivery to the dispensing apparatus, dose control, and/or microbial control between doses are desirable.

BRIEF SUMMARY

Liquid drug cartridges and associated inhalers are provided. In many embodiments, the cartridge includes a liquid drug container and a filter element. The filter element is configured to filter the liquid drug in the container prior to ejection from an ejection opening of the container. The cartridge includes a piston that is moved relative to the container to eject a volume of liquid from the container via the ejection opening. In many embodiments, the cartridge and associated inhaler are particularly suited for aerosolizing doses of insulin for pulmonary delivery. The liquid drug cartridge provides a convenient way of supplying liquid drug to an aerosol generator. In many embodiments, the combination of the cartridge and the associated inhaler provides improved control of dosage amount and improved suppression of microbial growth between doses.

Thus, in one aspect, a liquid drug cartridge is provided. The cartridge includes a container configured to store a liquid drug, an end cap coupled with a first end of the container, a filter element, and a piston. The end cap has an ejection opening from which a volume of the liquid drug from the container can be selectively ejected. The filter element is configured to filter the liquid drug prior to ejection from the ejection opening. The piston seals a second end of the container. The piston is repositionable relative to the container so as to selectively eject a volume of the liquid drug from the container via the ejection opening.

The cartridge can include additional elements and/or features. For example, the end cap can have a protruding portion in which the ejection opening is disposed. The cartridge can include a removable cap configured to interface with the end cap so as to block flow of the liquid drug through the ejection opening. The end cap can include a conduit in fluid communication with the ejection opening for delivery of the liquid drug to the ejection opening. The conduit can be coated to inhibit microbial ingress into the container. For example, the conduit can be coated with, or made from, silver to inhibit microbial ingress into the container.

The cartridge can be configured to inhibit escape of any amount of the liquid drug from the container absent repositioning of the piston relative to the container. For example, the conduit can be configured to inhibit escape of any amount of the liquid drug from the container absent repositioning of the piston relative to the container. For example, to prevent gravity induced flow of the liquid drug out of the cartridge in the absence of movement of the piston, the conduit can have a sufficiently small inner diameter relative to the surface tension and/or viscosity of the liquid drug so as to inhibit flow of the liquid drug through the conduit. The filter can also be configured to inhibit escape of any amount of the liquid drug from the container absent repositioning of the piston relative to the container.

The cartridge can be configured to inhibit microbial ingress into the container. For example, the conduit can be coated (e.g., with silver) to inhibit microbial ingress into the container. The filter element can also be configured to inhibit microbial ingress into the container. For example, the filter element can incorporate one or more antimicrobial materials and/or compounds (e.g., silver).

In another aspect, an aerosolization system is provided. The system can include any of the liquid drug cartridge embodiments described herein, an aerosol generator including a vibratable membrane having a front face and a rear face, a housing defining a mouthpiece, and an actuator configured to reposition the piston relative to the container to dispense a dosage of the drug via the ejection opening to the rear face of the vibratable membrane. The aerosol generator includes a vibratable element used to vibrate the vibratable membrane. The housing includes a receptacle configured to at least partially receive the cartridge and interface with the cartridge to position the ejection opening to dispense liquid drug directly onto the rear face of the vibratable membrane to be aerosolized by controlled vibration of the vibratable element.

The system can be configured such that the cartridge can be removed at any time to enable more thorough cleaning of the dispenser. When the cartridge is configured with a removable cap, the cap and the cartridge receiving receptacle can be configured such that the cartridge cannot be inserted into the receptacle until the cap is removed from the cartridge.

In many embodiments, the housing is configured to provide a mixture of air and aerosolized liquid drug for inhalation by a user. For example, the housing can include a mixing chamber in fluid communication with the front face of the vibratable membrane and the mouthpiece and one or more air inlets in fluid communication with the mixing chamber and configured to inlet air into the mixing chamber in response to a user inhaling via the mouthpiece. The system can further include an air flow restrictor array having greater resistance to air flow than the one or more air inlets and placing the mixing chamber in fluid communication with the one or more air inlets. In many embodiments, the restrictor array includes a plurality of orifices disposed in an annular arrangement. In many embodiments, the air flowing through the mixing chamber in response to the user inhaling via the mouthpiece is laminar and surrounds a dosage of the drug aerosolized via the vibratable membrane so as to inhibit contact between the aerosolized drug and surrounding surfaces of the mixing chamber. The system can include a pressure port connected to a pressure sensing system configured to detect a patient's inhalation.

The vibratable mesh can be coupled with the housing so as to enhance efficiency of the aerosol generator. For example, the vibratable mesh can be coupled with the housing via suitable isolator members, for example, elastomeric isolators.

The system can include an ultraviolet light source so as to provide microbial control between doses. For example, one or more ultraviolet lights sources can be used to irradiate a chamber of the housing disposed between the rear face of the vibratable member and the cartridge and into which the drug is ejected from the cartridge via the ejection opening.

In many embodiments, the housing is configured to retain the cartridge within the receptacle. Any suitable approach can be used to retain the cartridge within the receptacle. For example, the housing can be configured so as to form a pressurizable vessel that accommodates the cartridge. The actuator can be configured to pressurize the vessel to reposition the piston relative to the container to dispense a dosage of the drug via the ejection opening to the rear face of the membrane. Injection of air into the vessel can be controlled so as to dispense a predetermined desired amount of the liquid drug via the ejection opening for aerosolization by the aerosol generator. For example, the piston can be set slightly below the end of the container, creating a volume that can be pressurized by sealing against the end of the container or the inside wall of the container. As another example, the piston can be hollowed out on the side opposite the liquid drug to create a volume that can be pressurized. The pressurized volume will increase as liquid is dispensed. Removal (venting) of the air pressure can be used to immediately stop the piston from further movement until the air pressure is re-applied.

In many embodiments, the actuator mechanically displaces the piston relative to the container so as to dispense a predetermined desired amount of the liquid drug via the ejection opening for aerosolization by the aerosol generator. The actuator can include an adjustable metering mechanism that is operable to permit only selectable amounts of repositioning of the piston relative to the container so that a selectable dosage of the liquid drug is dispensed.

In many embodiments, the aerosolization system includes a control system configured to control various aspects of the system. For example, the system can include one or more processors and a tangible memory storing non-transitory instructions that, when executed by the one or more processors, cause the one or more processors to control the actuator to accomplish a priming cycle in which the actuator repositions the piston relative to the container until a drop of liquid has been ejected from the ejection opening. The instructions can be configured to cause the one or more processors to determine that a drop of the liquid has been ejected from the ejection opening by detecting when the vibratable member has been wetted by the ejected drop of the liquid drug.

A self-puncturing liquid drug cartridge and associated inhaler are also provided. In many embodiments, the cartridge includes a liquid drug container and a needle assembly coupled to the container. Upon insertion of the cartridge into the associated inhaler, a hollow needle of the needle assembly penetrates into the cartridge, thereby establishing a fluid path by which the liquid drug within the container can be ejected for aerosolizing by the inhaler. In many embodiments, the cartridge and associated inhaler are particularly suited for aerosolizing doses of insulin for pulmonary delivery. The self-puncturing liquid drug cartridge provides a convenient way of supplying liquid drug to an aerosol generator. In many embodiments, the combination of the cartridge and the associated inhaler provides improved control of dosage amount and improved suppression of microbial growth between doses.

Thus, in one aspect, a self-puncturing liquid drug cartridge is provided. The cartridge includes a container configured to store a liquid drug, a septum configured to seal a first end of the container; a needle assembly coupled to the first end of the container, and a piston sealing a second end of the container. The needle assembly includes a hollow needle and is reconfigurable between a first configuration in which the hollow needle does not extend through the septum and a second configuration in which the hollow needle extends through the septum. The piston is repositionable relative to the container so as to selectively eject a volume of the liquid drug from the container via the hollow needle.

In many embodiments, the needle assembly includes a cap configured to couple the needle assembly with the container. For example, the cap can include a receptacle shaped to receive and retain an end portion of the container (e.g., via complementarily-shaped surfaces providing a snap fit coupling between the cap and the end portion of the container). In many embodiments, the cap includes an aperture configured to accommodate a portion of the hollow needle and movement of the of the hollow needle during reconfiguration of the needle assembly from the first configuration to the second configuration. In many embodiments, there is an elastomeric seal disposed between the cap and the end portion of the container. The elastomeric seal prevents the liquid from leaking out from the container and prevents ingress of microbiological organisms and other contaminants.

In many embodiments, the needle assembly includes a guide element. The guide element can be configured to support the hollow needle in a fixed position and orientation relative to the guide element. The guide element can be configured to guide movement of the hollow needle relative to the container during reconfiguration of the needle assemble from the first configuration to the second configuration. The guide element can include a receptacle configured to receive the cap and a portion of the container and interface with at least one of the cap and the portion of the container so as to constrain relative movement between the container and the guide element to translation parallel to the hollow needle. In many embodiments, an end of the hollow needle from which the liquid drug is ejected protrudes from an end surface of the guide element by a predetermined controlled distance.

In many embodiments, the needle assembly includes a spring element configured to bias the needle assembly into the first configuration in the absence of induced displacement of the container relative to the guide element. For example, the needle assembly can include a coil spring disposed within the guide element receptacle and between an end wall of the guide element receptacle and the needle assembly cap. In the absence of induced displacement of the container and cap relative to the receptacle of the guide element, the spring is in an un-deformed configuration and the needle assembly is in the first configuration in which the hollow needle does not extend through the septum. By inducing displacement of the container and cap further into the receptacle of the guide element, the spring can be compressed sufficiently such that the needle assembly is reconfigured into the second configuration in which the hollow needle extends through the septum, thereby providing a fluid path for the liquid drug in the container to be ejected from the cartridge via the hollow needle.

In many embodiments, the guide element includes a feature to prevent the spring from pushing it off the cap. For example, the guide element can include a protruding feature on the inside surface of the guide element that slides in a slot on the outside surface of the cap. The slot can be further configured in the shape of a capital "L" to lock it in the first configuration for shipment. The patient would be required to twist the guide element before use to unlock it and allow the protruding feature to slide in the axial direction of the cap. Alternatively, the ends of spring can be mechanically fixed to the guide element and the cap to provide retention of these pieces. In many embodiments, the spring maintains a consistent and specific distance between the outlet of the needle and the back side of an aerosol generating mesh so as to prevent contact between the needle and the mesh but still close enough to transfer liquid droplets onto the mesh.

In many embodiments, the hollow needle is coated to inhibit microbial ingress into the hollow needle and the container. For example, the needle can be coated with silver to inhibit microbial growth and/or ingress. As another example, the self-puncturing liquid drug cartridge can include a filter configured to inhibit microbial ingress into the container.

In another aspect, an aerosolization system is provided. The system can include any of the self-puncturing liquid drug cartridge embodiments described herein, a housing defining a mouthpiece, an aerosol generator disposed in the housing, and an actuator configured to reposition the cartridge piston relative to the container to dispense a dosage of the liquid drug via the hollow needle to the aerosol generator. The housing includes a receptacle configured to at least partially receive the cartridge and interface with the needle assembly such that the needle assembly is reconfigured from the first configuration to the second configuration during an insertion of the cartridge into the receptacle. The aerosol generator includes a vibratable membrane having a front face and a rear face, and a vibratable element used to vibrate the membrane. The actuator is configured to reposition the piston relative to the container to dispense a dosage of the drug via the hollow needle to the rear face of the vibratable membrane. The system can be configured such that the cartridge can be removed at any time to enable more thorough cleaning of the dispenser. When the cartridge is configured with a removable cap, the cap and the cartridge receiving receptacle can be configured such that the cartridge cannot be inserted into the receptacle until the cap is removed from the cartridge.

In many embodiments, the housing is configured to provide a mixture of air and aerosolized liquid drug for inhalation by a user. For example, the housing can include a mixing chamber in fluid communication with the front face of the vibratable membrane and the mouthpiece and one or more air inlets in fluid communication with the mixing chamber and configured to inlet air into the mixing chamber in response to a user inhaling via the mouthpiece. The system can further include an air flow restrictor array having greater resistance to air flow than the one or more air inlets and placing the mixing chamber in fluid communication with the one or more air inlets. In many embodiments, the restrictor array includes a plurality of orifices disposed in an annular arrangement. In many embodiments, the air flowing through the mixing chamber in response to the user inhaling via the mouthpiece is laminar and surrounds a dosage of the drug aerosolized via the vibratable membrane so as to inhibit contact between the aerosolized drug and surrounding surfaces of the mixing chamber. The system can include a pressure port connected to a pressure sensing system configured to detect a patient's inhalation.

The vibratable mesh can be coupled with the housing so as to enhance efficiency of the aerosol generator. For example, the vibratable mesh can be coupled with the housing via suitable isolator members, for example, elastomeric isolators.

The system can include an ultraviolet light source so as to provide microbial control between doses. For example, one or more ultraviolet lights sources can be used to irradiate a chamber of the housing disposed between the rear face of the vibratable member and the cartridge and into which the drug is ejected from the cartridge via the hollow needle.

In many embodiments, the housing is configured to retain the cartridge within the receptacle. Any suitable approach can be used to retain the cartridge within the receptacle. For example, the housing can be configured so as to form a pressurizable vessel that accommodates the cartridge. The actuator can be configured to pressurize the vessel to reposition the piston relative to the container to dispense a dosage of the drug via the hollow needle to the rear face of the membrane. Injection of air into the vessel can be controlled so as to dispense a predetermined desired amount of the liquid drug via the hollow needle for aerosolization by the aerosol generator. For example, the piston can be set slightly below the end of the container, creating a volume that can be pressurized by sealing against the end of the container or the inside wall of the container. As another example, the piston can be hollowed out on the side opposite the liquid drug to create a volume that can be pressurized. The pressurized volume will increase as liquid is dispensed. Removal (venting) of the air pressure can be used to immediately stop the piston from further movement until the air pressure is re-applied.

In many embodiments, the actuator mechanically displaces the piston relative to the container so as to dispense a predetermined desired amount of the liquid drug via the hollow needle for aerosolization by the aerosol generator. The actuator can include an adjustable metering mechanism that is operable to permit only selectable amounts of repositioning of the piston relative to the container so that a selectable dosage of the liquid drug is dispensed.

In many embodiments, the aerosolization system includes a control system configured to control various aspects of the system. For example, the system can include one or more processors and a tangible memory storing non-transitory instructions that, when executed by the one or more processors, cause the one or more processors to control the actuator to accomplish a priming cycle in which the actuator repositions the piston relative to the container until a drop of liquid has been ejected from the hollow needle. The instructions can be configured to cause the one or more processors to determine that a drop of the liquid has been ejected from the hollow needle by detecting when the vibratable member has been wetted by the ejected drop of the liquid drug.

BRIEF DESCRIPTION OF THE DRAWINGS

FIG. 9 is a partial cut-away side view of a self-puncturing liquid drug cartridge, in accordance with many embodiments.

FIG. 10 is a partial cross-sectional side view of a removable cap coupled with an end of the drug cartridge of FIG. 9, in accordance with many embodiments.

DETAILED DESCRIPTION

Figure 1:
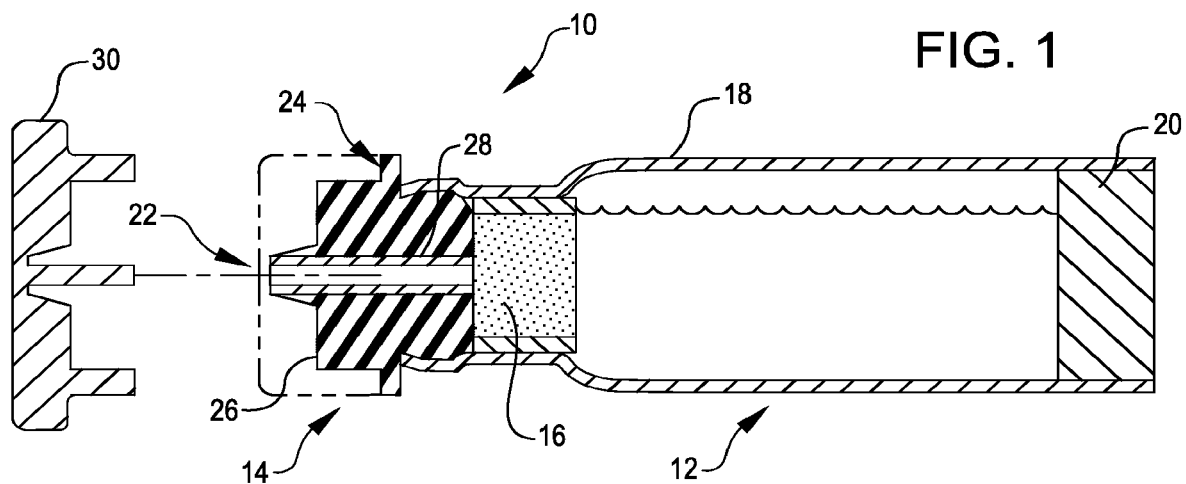
FIG. 1 is a cross-sectional view of a liquid drug cartridge, in accordance with many embodiments.

Liquid drug cartridges and an associated inhaler are described herein. In many embodiments, a cartridge containing a drug formulation is inserted into a dispenser until the cartridge contacts a shelf of the dispenser. In many embodiments, a continuous dispensing of formulation is possible, as well as very small and very large doses from the same cartridge.

The cartridge can be biased into contact with a mating surface of the inhaler to ensure precise and close positioning of the ejection opening relative to a vibratable membrane of the inhaler so that when a droplet of liquid drug is dispensed via the ejection opening, surface tension will cause it to it will adhere to the vibratable membrane even when the inhaler is in a horizontal orientation. The adherence is controlled by the distance between the ejection opening and vibratable membrane, the inside diameter of the ejection opening, and the geometry of the ejection opening where the droplet exits.

The membrane vibrates to generate an aerosol and creates a pumping action that pulls the droplet away from the ejection opening and through the membrane. At the end of a dose, there is no residual droplet to be aerosolized due to the pumping action of the membrane. In many embodiments, elastomeric isolators are used to couple the vibratable membrane with a housing of the inhaler to maximize efficiency of the aerosol generation.

In many embodiments, as the patient inhales, air flows through air inlets into a manifold and then passes through a restrictor array. The air flow transports the aerosol to the patient. In many embodiments, the air inlet have significantly less resistance than the restrictor array. A pressure port and associated pressure sensor can be incorporated to detect the strength of a patient's inhalation.

The cartridge can be configured to inhibit microbial ingress into the liquid drug container. For example, the end cap can include a conduit that is coated, for example with silver, to discourage microbial ingress into the conduit and the liquid drug container. In many embodiments, there is no retrograde flow back into the container after a dose is dispensed (i.e., any drug in the conduit there in contact with the antimicrobial coating to suppress pathogen proliferation). The liquid drug cartridge can include a filter configured to inhibit microbial ingress into the container.

The cartridge is configured to protect the user against accidental needle stick. For example, the ejection opening can be integrally formed into the end cap, thereby avoiding the use of a needle. A removable protective cap can be used to protect the ejection opening from damage and contamination. The protective cap can be shaped such that that the cartridge cannot be inserted into the inhaler until the protective cap is removed.

The cartridge include a piston slidably disposed within the container for dispensing the liquid drug without the introduction of air. This feature improves physical stability of the drug product, supports use of the cartridge in a horizontal orientation, and maintains the container in a sealed configuration at all times for consistent dosing.

Any suitable approach for actuating the piston can be used. For example, the piston can be air driven by incorporating a seal between the end member and the housing of the inhaler or it can be mechanically driven via an actuation mechanism coupled with the end member or passing through the end member.

A priming cycle can be used to eject air from the container and/or the ejection opening. For example, after a cartridge is loaded into an associated inhaler, a mechanical plunger can be brought into contact with and push the piston until a drop of formulation is dispensed. This can be sensed by aerosol generator software, which can be configured detect the difference between a wet and dry vibratable membrane.

An inhaler can incorporate additional microbial control features. For example, an ultraviolet light can be added in a chamber where the droplet is ejected from the ejection opening so as to provide additional microbial control between doses.

The cartridge and the inhaler can be configured such that the cartridge can be removed and reinserted at any time. For example, the cartridge can be removed at any time to enhance access for cleaning the inhaler. In many embodiments, reinsertion of the cartridge induces a priming cycle.

In many embodiments, an inhaler includes a housing defining a dispensing outlet, a vibratable membrane having a front face exposed at the outlet and a rear face for receiving a liquid to be dispensed, and a vibrating mechanism connected to the housing and operable to vibrate the membrane to dispense aerosol of the liquid through the membrane. A liquid delivery system is used to deliver a metered quantity of the liquid to the rear face of the membrane. In this way, a metered quantity of liquid is dispensable at the outlet by operating the vibrating mechanism for an operating period sufficient to completely aerosolize the metered quantity of liquid delivered to the rear face of the vibratable member.

An advantage of such an apparatus is that it facilitates the dispensing of substantially all of the liquid coming into contact with the rear face of the membrane as a single dose, especially when the metered dose is relatively small in volume. By dispensing the entire dose, the membrane is essentially free of liquid from one dose to the next. In this way, it is thereby possible to avoid contact between liquid and ambient air during periods of non-use between successive uses. For pharmaceutical preparations this is particularly important since it may obviate the need for the use of preservatives in the liquid and avoids evaporative losses. For example, various preservative free insulin formulations that may be used include those described in U.S. application Ser. No. 13/004,662, entitled "Preservative Free Insulin Formulations and Systems and Methods for Aerosolizing" and in U.S. Provisional Application No. 62/120,573, entitled "Liquid Insulin Formulations," each of which is hereby incorporated by reference in its entirety.

Such an apparatus is particularly useful in the administration of inhaled pharmaceutical liquid products where it is required that a fine aerosol of liquid be entrained in an inhaled air flow passing through the mouthpiece. One example of such a liquid is an insulin composition.

In many embodiments, the cartridge is a multi-dose cartridge. For example, the cartridge may contain enough medication for a day, a week, or a month's worth of treatment. The volume of the dose dispensed from the cartridge can be controlled via any suitable approach, such as via positioning of the piston. The position of movement of the piston can be set by an external control. For example, the piston can be moved in small enough increments to eject a very small volume of liquid, for example 10 µL of liquid, or a large volume of liquid, for example 1000 µL of liquid, thereby delivering a small or large amount of medication. The position of the piston can be maintained in a fixed location after dosing, until a future dose is required. To dispense subsequent doses, the piston can be moved through subsequent positions to deliver additional doses until the cartridge is empty.

Turning now to the drawings in which like numbers reference like components, FIG. 1 illustrates a liquid drug cartridge 10, in accordance with many embodiments. The liquid drug cartridge 10 includes a container assembly 12, an end cap assembly 14, and a filter 16.

The container assembly 12 is configured to store a liquid drug for subsequent dispensing to an inhaler. The container assembly 12 includes a container 18 having openings at opposing ends of the container 18. The end cap assembly 14 seals a first end of the container 18. A piston 20 seals a second end of the container 18. The piston 20 is selectively slidable within the container 18 so as to eject a selected quantity of the liquid drug from the container 18.

The end cap assembly 14 has an ejection opening 22 from which the liquid drug is ejected. In many embodiments, the end cap assembly 14 is configured so that the ejection opening 22 is located at the end of a protruding portion of the end cap assembly 14 so as to be located at a precise location relative to an interface surface 24 of the end cap assembly 14.

The end cap assembly 14 includes an end cap body 26, a conduit 28, and a removable cover 30. The cover 30 can be configured to provide a microbial barrier prior to the first use of the cartridge. This microbial barrier could be achieve by sealing against the end cap assembly 14 or by integrating the cover 30 and end cap assembly 14 into the one piece that is separated as the cap is removed. The end cap body 26 can be made from a suitable material (e.g., a suitable resilient material) and be shaped to interface with complementarily shaped end portion of the container 18. In the illustrated embodiment, the conduit 28 is a cylindrical metal component having a suitable inside diameter. For example, the inside diameter of the conduit 28 can be selected to be large enough to allow controlled flow of the liquid drug when the piston is controllably displaced relative to the container 18 yet small enough to inhibit flow of the liquid drug in the absence of movement of the piston 20 relative to the container 18.

The filter 16 is configured to filter the liquid drug ejected from the container 18 prior to passing through the conduit 28. In the illustrated embodiment, the filter 16 has a cylindrical body made from a suitable filter material. For example, a sintered polyethylene filter with pore size of 0.2 to 100 µm or a thin membrane composed of Nylon, PTFE, polypropylene, or other material that is compatible with the liquid drug cartridge 10. This filter may be designed to resemble a syringe filter. Controlled movement of the piston 20 relative to the container 18 is used to induce flow of the liquid drug in the container through the filter 16. After passing through the filter 16, the liquid drug passes through the conduit 28 to exit via the ejection opening 22. The filter 16 can be configured to inhibit flow of the liquid drug into the conduit 28 in the absence of movement of the piston relative to the container 18.

Figure 2:
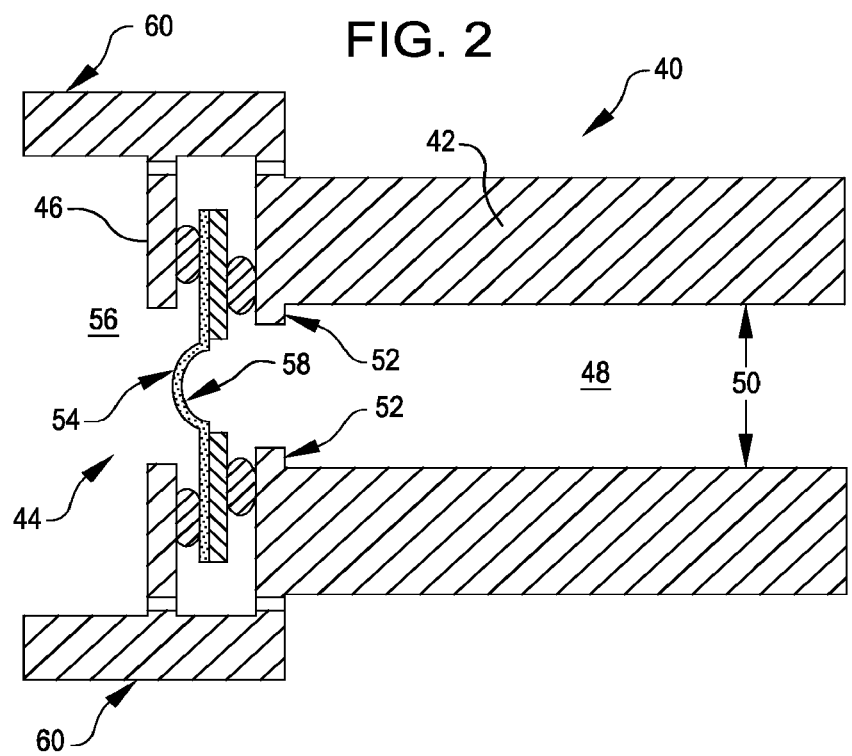
FIG. 2 is a cross-sectional view illustrating an inhaler into which a drug cartridge is inserted, in accordance with many embodiments.

FIG. 2 shows a cross-sectional view of an inhaler 40, in accordance with many embodiments, that is configured to use the liquid drug cartridge 10. The inhaler 40 includes a housing 42 and an aerosol generator 44 mounted to the housing 42 via isolators 46. The housing 42 forms a receptacle 48 configured to slidingly receive the liquid drug cartridge 10. An inner surface 50 of the receptacle 48 is configured to interface with the exterior surface of the liquid drug cartridge 10 such that the liquid drug cartridge 10 is constrained to slidingly translate relative to the receptacle 48. The interface surface 24 of the end cap assembly 14 contacts a shelf 52 of the inhaler 40 so as to position the ejection opening 22 in a fixed position relative to the aerosol generator 44.

The aerosol generator 44 includes a vibratable membrane having a front face 54 exposed to an outlet duct 56 and a rear face 58 contacted in use by liquid ejected from the liquid drug cartridge 10. The aerosol generator 44 is mounted to the housing 42 by the isolators 46 and is operable to dispense an active pharmaceutical agent as an aerosol through a mouthpiece 60. Exemplary aerosol generators that can be used are also described in U.S. Pat. Nos. 5,164,740; 6,629,646; 6,926,208; 7,108,197; 5,938,117; 6,540,153; 6,540,154; 7,040,549; 6,921,020; 7,083,112; 7,628,339; 5,586,550; 5,758,637; 6,085,740; 6,467,476; 6,640,804; 7,174,888; 6,014,970; 6,205,999; 6,755,189; 6,427,682; 6,814,071; 7,066,398; 6,978,941; 7,100,600; 7,032,590; 7,195,011, incorporated herein by reference. These references describe exemplary aerosol generators, ways to manufacture such aerosol generators and ways to supply liquid to aerosol generators, and are incorporated by reference for at least these features. The aerosol generators may comprise vibratable membranes having tapered aperture with a size in the range from about 3 µm to about 8 µm, preferably from about 3 µm to about 6 µm, and in some cases around 4 µm. The membrane may be domed shaped and be vibrated by an annular piezoelectric element that circumscribes the apertures. The diameter of the membrane may be in the range from about 5 mm to about 8 mm. The membrane may also have a thickness in the range from about 50 microns to about 70 microns. Typically, the membrane will be vibrated at a frequency in the range from about 50 kHz to about 150 kHz.

Figure 3:
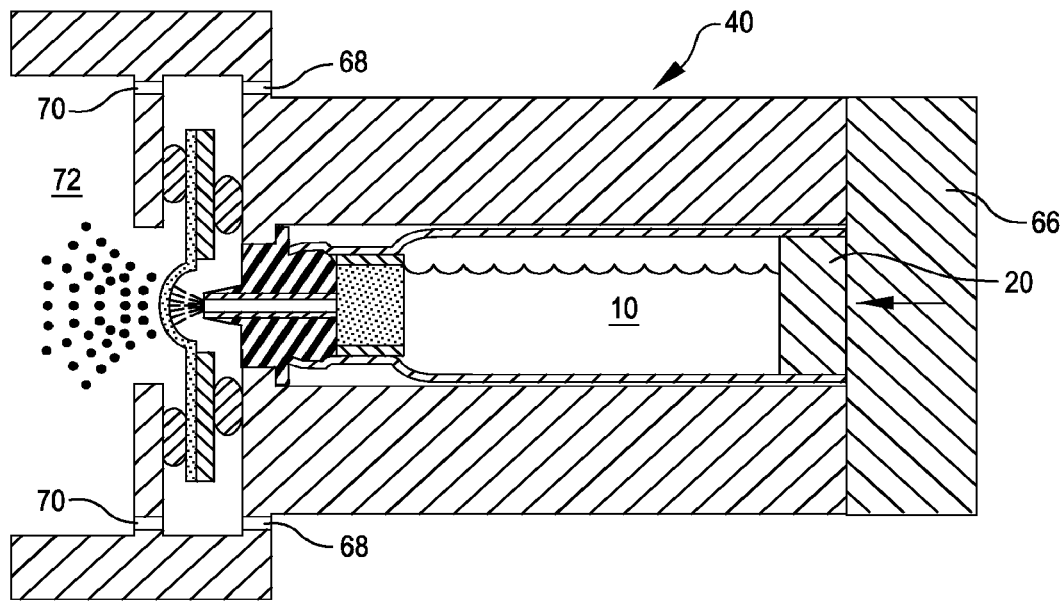
FIG. 3 is a cross-sectional view illustrating the drug cartridge of FIG. 1 inserted into the inhaler of FIG. 2 and retained by an end member, as well as liquid drug ejected from the cartridge being aerosolized for inhalation by a user, in accordance with many embodiments.

FIG. 3 illustrates the liquid drug cartridge 10 installed into the inhaler 40. An end member 66 retains the liquid drug cartridge 10 so as to maintain contact between the interface surface 24 of the end cap assembly 14 and the shelf 52 of the inhaler 40, thereby precisely controlling the position of the ejection opening 22 relative to the rear face 58 of the vibratable membrane.

The inhaler 40 can include a suitable actuator for displacing the piston 20 relative to the container 18 so as to eject a desired preselected dose of liquid drug from the container 18 via the ejection opening 22. For example, the end member 66 and the housing 42 can form a pressurizable vessel into which air can be injected so as to displace the piston 20 towards the ejection opening 22. As another example, the piston 20 can be controllably displaced toward the ejection opening 22 via an actuation mechanism coupled with the end member 66 or acting through the end member 66.

In use, a user inhales from the mouthpiece 60 and the aerosol generator 44 simultaneously aerosolizes a dose of liquid drug ejected from the ejection opening 22 via a corresponding actuation of the piston 20. The housing 42 includes one or more air inlets 68 and a restrictor array 70 by which air is introduced into a mixing chamber 72 for combination with the aerosolized dose of the liquid drug prior to inhalation by the user.

Figure 4:
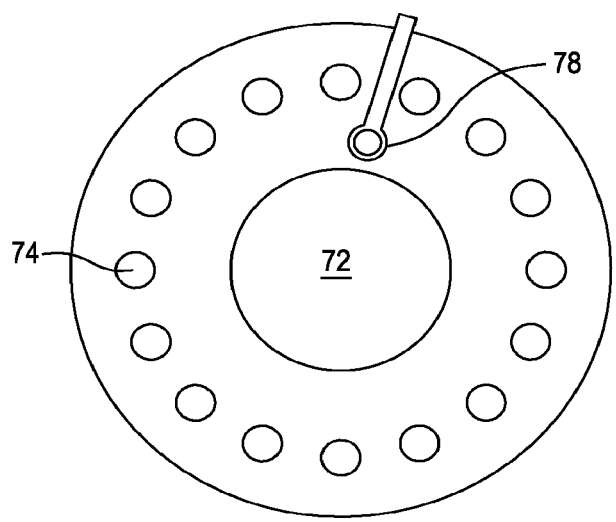
FIG. 4 is an end view illustrating a flow restricting array of orifices of the inhaler of FIG. 2, in accordance with many embodiments.

FIG. 4 shows an end view of the restrictor array 70, which includes an annular arrangement of orifices 74. The orifices 74 are sized such that the user inhalation occurs over a sufficient period of time for the liquid drug dose to be suitably aerosolized. In many embodiments, the one or more air inlets 68 have significantly less resistance to airflow than the restrictor array 70. In many embodiments, the restrictor array 70 is configured to produce laminar airflow that surrounds the resulting flow of the aerosolized liquid drug, thereby inhibiting and even largely preventing contact between the aerosolized drug and surfaces of the mixing chamber 72.

In many embodiments, the inhaler 40 includes an ultraviolet light source configured to illuminate at least a portion of a chamber (not shown; similar to mixing chamber 72) into which the ejecting end of the hollow needle (not shown; similar to hollow needle 316) ejects the liquid drug. The ultraviolet light source can be used to provide increased microbial control, for example, in the time periods between doses.

In many embodiments, the inhaler 40 includes a pressure port 78 that is coupled to a pressure sensing system to detect a patient's inhalation. For example, the pressure sensor can be used to determine when a patient starts breathing so as to start the aerosol generator and when the patient stops breathing so as to pause generation to prevent waste, maximize dose efficiency, and maintain consistent delivery.

Figure 5:
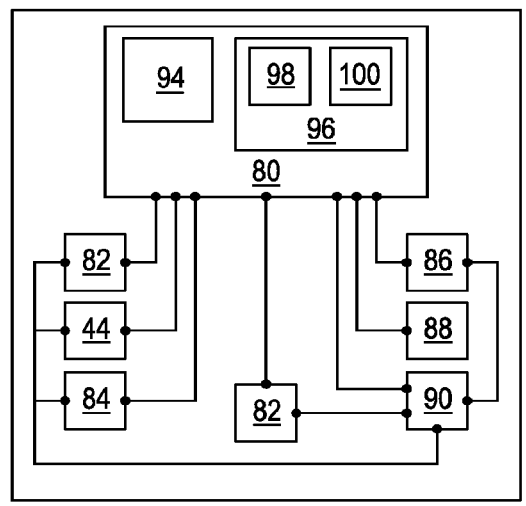
FIG. 5 is a simplified schematic diagram illustrating components of an inhaler configured to receiving liquid drug from a drug cartridge, in accordance with many embodiments.
Figure 6:
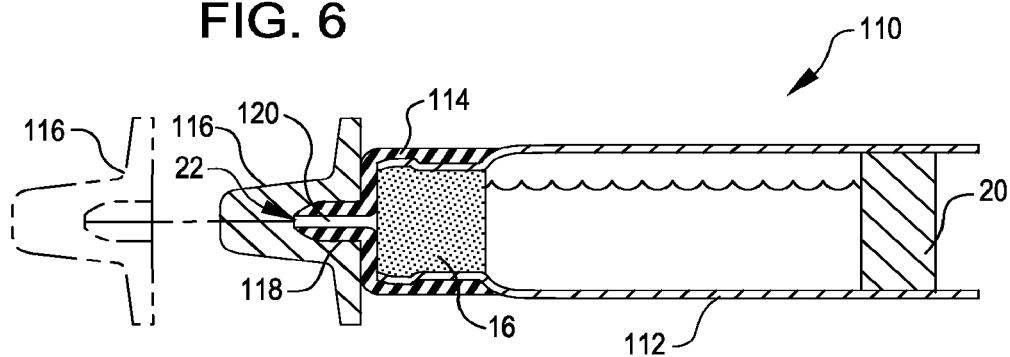
FIG. 6 is a cross-sectional view of another liquid drug cartridge, in accordance with many embodiments.
Figure 7:
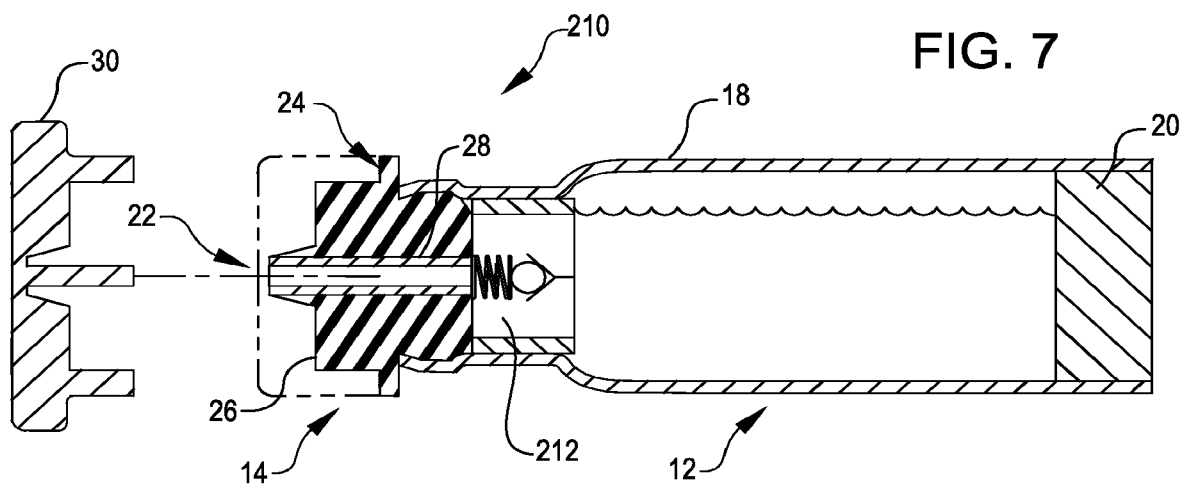
FIG. 7 is a cross-sectional view of a liquid drug cartridge that includes a check valve, in accordance with many embodiments.
Figure 8:
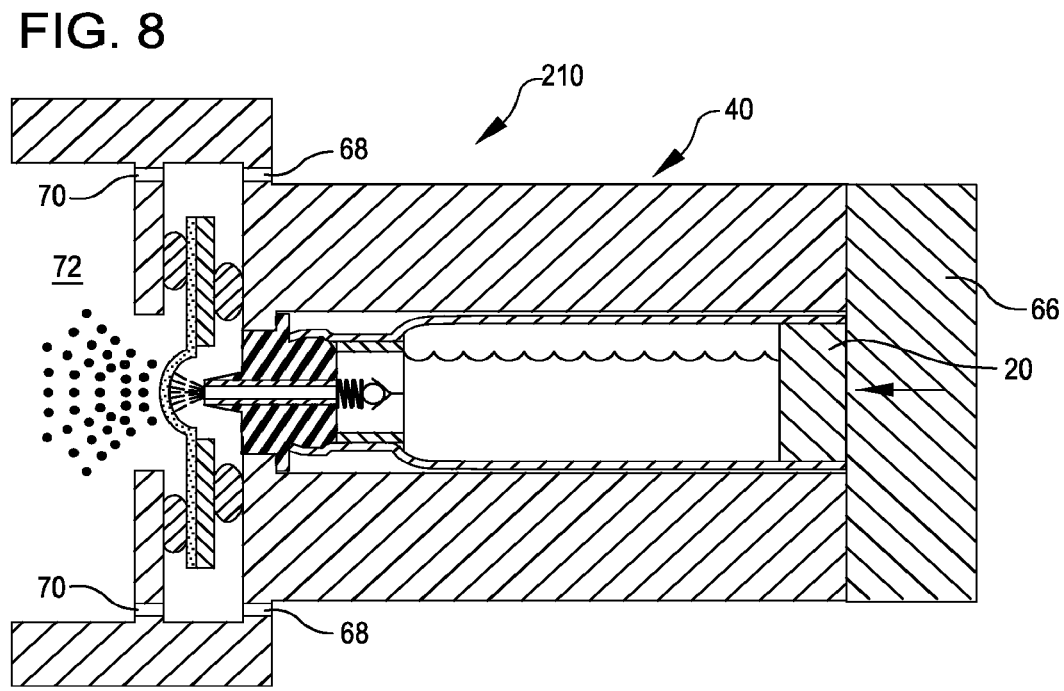
FIG. 8 is a cross-sectional view illustrating the drug cartridge of FIG. 7 inserted into the inhaler of FIG. 2, as well as liquid drug ejected from the cartridge being aerosolized for inhalation by a user, in accordance with many embodiments.

FIG. 5 shows a simplified schematic diagram of components of the inhaler 40. The inhaler 40 includes control electronics 80, input/output device(s) 82, the aerosol generator 44, an inhalation strength monitoring system 84, an ultraviolet light source 86, a piston actuation system 88, one or more batteries 90, and/or an external port 92. The control electronics 80 are operatively coupled with the input/output device(s) 82, the aerosol generator 44, the inhalation strength monitoring system 84, the ultraviolet light source 86, the piston actuation system 88, the one or more batteries 90, and/or the external port 92.

Any suitable configuration of the control electronics 80 can be used. For example, in the illustrated embodiment, the control electronics 80 include one or more processors 94 and a tangible memory 96. The memory 96 can include read only memory (ROM) 98 and/or random access memory (RAM) 100. The memory 96 stores instructions that, when executed by the one or more processors 94, cause the processor(s) to control the operation of the various subsystems of the inhaler 40.

For example, the instructions can be configured to cause the control electronics 80 to receive input from a user via the input/output devices 82 regarding a desired dose of liquid drug to be dispensed by the inhaler 40. The control electronics 80 can receive a signal from the inhalation strength monitoring system 84 indicative of inhalation via the inhaler 40 by the user. In response to the signal indicating inhalation by the user, the control electronics can cause the piston actuation system 88 to eject a dose of liquid drug to the aerosol generator 44 and cause the aerosol generator 44 to aerosolize the ejected dose concurrent with the detected inhalation by the patient. In response to the signal indicating when the patient stops inhaling, the control electronics can be configured to pause the aerosol generation.

Any suitable configuration of the input/output device(s) 82 can be used. For example, the input/output device(s) 82 can include input buttons and a display device, such as an LCD screen and/or one or more indicator lights.

The inhalation strength monitoring system 84 can include a pressure transducer operatively coupled to the pressure port 78. The pressure transducer outputs a signal to the control electronics 80 indicative of the pressure at the pressure port 78. The control electronics 80 can be configured to monitor the pressure signal from the pressure transducer so as to detect reduced pressure associated with airflow through the inhaler induced by a user's inhalation.

The ultraviolet light source 86 can be energized periodically for any suitable length of time so as to provide microbial control between doses. The ultraviolet light source can be selected to provide an appropriate wavelength spectrum to kill microbes. For example, the control electronics 80 can be configured to energize the ultraviolet light source 86 in accordance with a predetermined schedule following the administration of any particular dose.

The one or more batteries 90 can be connected to the various subsystems of the inhaler in any suitable fashion. For example, the one or more batteries 90 be directly wired any particular subsystem with the control electronics 80 being connected to control an associated switch used to control the supply of power from the one or more batteries 90 to the particular subsystem. The one or more batteries 90 can be replaceable and/or rechargeable.

In embodiments where the one or more batteries 90 are rechargeable, recharging can be accomplished via the external port 92. The external port 92 can also be used to transfer data to and/or from the control electronics 80, for example, program instructions and/or operational parameters for operational control of the inhaler 40 and/or inhaler use data that is output to an external system for review and/or analysis.

The inhaler 40 can be operated to deliver a metered quantity of the liquid drug from the liquid drug cartridge 10 to the rear face 58 of the vibratable membrane 64. Hence, for each use a metered quantity of aerosolized pharmaceutical agent can be dispensed at the mouthpiece 60 outlet by operation of the aerosol generator 44.

The liquid drug cartridge 10 contains a reservoir of active pharmaceutical agent, from which a predetermined does of the agent can be dispensed. For example, a dose of between about 80 to about 120 micro-liters of insulin. The lower limit is typically at least about 15 micro-liters and the upper limit is typically about 1,000 micro-liters to about 2,000 micro-liters. One particularly useful range is about 80 micro-liters to about 120 micro-liters in a concentration of about 100 insulin units/ml or greater, and more preferably between about 200-800 units/ml, and in some cases as high as 2,500 units/ml.

The conduit 28 provides a fluid passage for the liquid drug to the vibratable membrane 64. The ejection opening 22 is positioned in closed proximity to rear face 58 of the vibratable membrane 64. Typically, the ejection opening 22 will be less than 5 mm and more preferably less than 2 mm from the rear face 58. The conduit 28 can be made of, for example, stainless steel alloy type 316 with a gage size ranging from 22 gage to 26 gage.

When the liquid drug cartridge 10 is installed in the inhaler 40, an indicator light can start to blink signaling to the patient that the inhaler 40 is ready for use. At any time shortly thereafter the patient may inhale through the mouthpiece 60. Patient inhalation is detected by a flow sensor. The detection of patient inhalation results in activation of the aerosol generator 44 to produce aerosol particles into the mixing chamber 72. Aerosol is entrained in the inhalation air flow and flows via the respiratory system to the lungs of the patient. When the entire dose is aerosolized, which may take one or more breaths, an "end-of-dose" indicator light can be illuminated a second time to signal the patient that the entire dose has been delivered. Delivery of the entire dose is obtained when at least about 95% of the dose is delivered, more preferably 98% and most preferably when more than 99% of the dose is delivered. To receive the dose, the patient may take several inhalations or a single inhalation depending on the volume of liquid drug delivered to the vibratable membrane 64 and the patient's breathing capacity. Each inhalation should be a deep breath to assure that the aerosol reaches deeply to the lungs.

The inhaler can be configured to accommodate cleaning and/or sterilization of the vibratable membrane and/or the chamber into which the liquid drug cartridge 10 ejects the liquid drug. The inhaler can include air vents and/or drain features so that a cleaning fluid (e.g., water or any suitable fluid) can be introduced to and removed from the chamber into which the liquid drug cartridge 10 ejects the liquid drug. The control electronics can be sealed in one or more separate compartments to avoid contact with the cleaning fluid. A cleaning cartridge containing a cleaning fluid (e.g., water or any suitable fluid) can be occasionally installed to clean the mesh. The pressure sensing can be reversed to turn the inhaler off if someone tries to inhale the water vapor. There can be a "soak" mode where the water droplet is allow to sit on the mesh with an occasional vibration, for example, providing an alternating soak, rinse, soak, rinse cycle. A simpler configuration would employ a plastic funnel with a small opening at the tip that the patient would insert into the cartridge slot and drip water into the inhaler. The small opening can be configured to limit the amount of water to a slow drip.

FIG. 6 illustrates another liquid drug cartridge 110, in accordance with many embodiments, that can be used with an inhaler (e.g., the inhaler 40). The liquid drug cartridge 110 includes a container 112, a filter 16, an end cap 114, and a removable cover 116. The end cap 114 has a protruding portion 118 that provides a conduit 120 for fluid and an ejection opening 22 from which the liquid drug is ejected to the rear face 58 of the vibratable membrane 64. As with the conduit 28, the inside diameter of the conduit 120 can be selected to be large enough to allow controlled flow of the liquid drug when the piston 20 is controllably displaced relative to the container 112 yet small enough to inhibit flow of the liquid drug in the absence of movement of the piston 20 relative to the container 112. The inside of the conduit 120 can be coated (e.g., with silver) to inhibit the ingress of microbes into the liquid drug cartridge 110.

FIG. 7 illustrates another liquid drug cartridge 210, in accordance with many embodiments. The liquid drug cartridge 210 is configured similar to the cartridge 10 but includes a check valve 212 in addition to the container assembly 12 and the end cap assembly 14 described herein with respect to the liquid drug cartridge 10. Although not included in the illustrated embodiment, the liquid drug cartridge 210 can further include a filter element such as the filter element of the liquid drug cartridge 10. For example, one or more filters the same or similar to the filter 16 can be disposed upstream of the check valve 212 and/or downstream of the check valve 212.

In many embodiments, the check valve 212 is configured to provide a physical barrier against microbial ingress into the liquid drug stored within the container 18. Any suitable configuration can be used for the check valve 212 to ensure only one-way flow of the liquid drug from the container 18 to the conduit 28. For example, the check valve 212 can be a duckbill valve or a mechanical valve such as a spring loaded ball valve. Opening and closing of the check valve 212 can be controlled by pressure within the container 18 as a result of actuation of the piston 20 as described herein. The check valve 212 can be mechanically actuated and/or electrically actuated. Example suitable check valve configurations that can be employed are described in U.S. Pat. Nos. 5,759,101 and 6,089,260; and in U.S. Patent Publications 2015/0048119 and 2012/0041381; the full disclosures of which are hereby incorporated by reference herein.

FIG. 8 illustrates the liquid drug cartridge 210 installed into the inhaler 40. The end member 66 retains the liquid drug cartridge 210 so as to maintain contact between the interface surface 24 of the end cap assembly 14 and the shelf 52 of the inhaler 40, thereby precisely controlling the position of the ejection opening 22 relative to the rear face 58 of the vibratable membrane.

As described herein, in many embodiments the inhaler 40 is configured to controllably displace the piston 20 relative to the container 18. Displacing the piston 20 relative to the container 18 can be used to increase the pressure within the container 18 so as to open the check valve 212 to eject a desired preselected dose of liquid drug from the container 18 via the ejection opening 22 for inhalation by a user as described herein.

Self-Puncturing Liquid Drug Cartridges

Embodiments of self-puncturing liquid drug cartridges are also described herein. In many embodiments, a self-puncturing liquid drug cartridge containing a drug formulation is inserted into a dispenser until a guide element of the cartridge contacts a shelf of the dispenser. When the cartridge is further inserted into the dispenser, a cap and container assembly of the cartridge slides inside the guide element and against the sharpened end of a hollow needle of the cartridge. The hollow needle punctures a septum so as to establish a fluid path for ejection of the liquid drug from the container of the cartridge for aerosolization by the inhaler for inhalation by a user. In many embodiments, a continuous dispensing of formulation is possible, as well as very small and very large doses from the same cartridge.

The cartridge includes a spring that assures that the guide element remains in contact with the shelf after the cartridge is fully inserted into the inhaler and retained by an end member of the inhaler. The shelf provides precise and close positioning of the hollow needle relative to a vibratable membrane of the inhaler so that when a droplet of liquid drug is dispensed via the hollow needle, surface tension will cause it to it will adhere to the vibratable membrane even when the inhaler is in a horizontal orientation. The adherence is controlled by the distance between the hollow needle and vibratable membrane, the inside diameter of the hollow needle, and the geometry of the hollow needle where the droplet exits.

The membrane vibrates to generate an aerosol and creates a pumping action that pulls the droplet away from the hollow needle and through the membrane. At the end of a dose, there is no residual droplet to be aerosolized due to the pumping action of the membrane. In many embodiments, elastomeric isolators are used to couple the vibratable membrane with a housing of the inhaler to maximize efficiency of the aerosol generation.

The hollow needle can be coated, for example with silver, to discourage microbial ingress into the hollow needle and the liquid drug container. In many embodiments, there is no retrograde flow back into the container after a dose is dispensed (i.e., any drug in the needle stays there in contact with the antimicrobial coating to suppress pathogen proliferation). The self-puncturing liquid drug cartridge can include a filter configured to inhibit microbial ingress into the container.

The cartridge is configured to protect the user against accidental needle stick. Only one end of the hollow needle is sharpened and the guide element supports and encloses the hollow needle such that the sharp end of the hollow needle is not exposed and is directed towards the septum. The exposed end of the hollow needle is not sharpened. A removable protective cap protects the exposed end of the hollow needle from damage and contamination. The protective cap is shaped such that that the cartridge cannot be inserted into the inhaler until the protective cap is removed.

The cartridge include a piston slidably disposed within the container for dispensing the liquid drug without the introduction of air. This feature keeps the hollow needle submerged for the duration of dispensing, improves physical stability of the drug product, supports use of the cartridge in a horizontal orientation, and maintains the container in a sealed configuration at all times for consistent dosing.

The cartridge and the inhaler can be configured such that the cartridge can be removed and reinserted at any time. For example, the cartridge can be removed at any time to enhance access for cleaning the inhaler. In many embodiments, reinsertion of the cartridge induces a priming cycle. In such embodiments, the septum can be configured to be punctured multiple times without compromising the sterility of the container.

FIG. 9 illustrates a self-puncturing liquid drug cartridge 310, in accordance with many embodiments. The self-puncturing liquid drug cartridge 310 includes a container assembly 312 and a needle assembly 314, which is coupled to the container assembly 312 and includes a hollow needle 316.

The container assembly 312 is configured to store a liquid drug for subsequent dispensing to an inhaler. The container assembly 312 includes a container 318 having openings at opposing ends of the container 318, a septum 320 sealing a first end of the container 318, and a piston 322 sealing a second end of the container 318. The septum 320 is configured to be punctured by the hollow needle 316 to establish a fluid path by which the liquid drug within the container 318 can be dispensed to an inhaler. The piston 322 is selectively slidable within the container 318 so as to eject a selected quantity of the liquid drug from the container 318 via the hollow needle 316.

The needle assembly 314 is reconfigurable between a first configuration (illustrated in FIG. 9) in which the hollow needle 316 does not extend through the septum 320 and a second configuration (see, e.g., FIG. 13) in which the hollow needle 316 extends through the septum 320. The needle assembly 314 includes the hollow needle 316, a cap 324, a guide element 326, and a spring 328. In the illustrated embodiment, the cap 324 is configured to couple the needle assembly 314 to the container assembly 312. Any suitable approach can be used to couple the needle assembly 314 with the container assembly 312. For example, in the illustrated embodiment, the cap 324 is configured to receive a first end portion of the container assembly 312 and retain the received portion via complementary snap fit features of the cap 324 and the container assembly 312. The guide element 326 includes a receptacle 330 configured to slidingly receive and interface with the cap 324 and a portion of the container assembly 312. Opposing ends of the spring 328 are coupled with an end wall 332 of the receptacle 330 and the cap 324, respectively. In the first configuration, the spring 328 is in an un-deflected configuration and maintains the illustrated separation between the cap 324 and the end wall 332 of the receptacle 330, thereby disposing the hollow needle 316 in the position illustrated relative to the septum 320. The guide element 326 has an exterior surface 334 and an exterior end wall surface 336.

FIG. 10 illustrates a removable protective cover 362 coupled with the self-puncturing liquid drug cartridge 310. The removable protective cover 362 protects the hollow needle 316 from damage and contamination. The removable protective cover 362 is shaped to prevent insertion of the self-puncturing drug cartridge 310 into the inhaler 40 until the removable protective cover 362 is removed.

Figure 11:
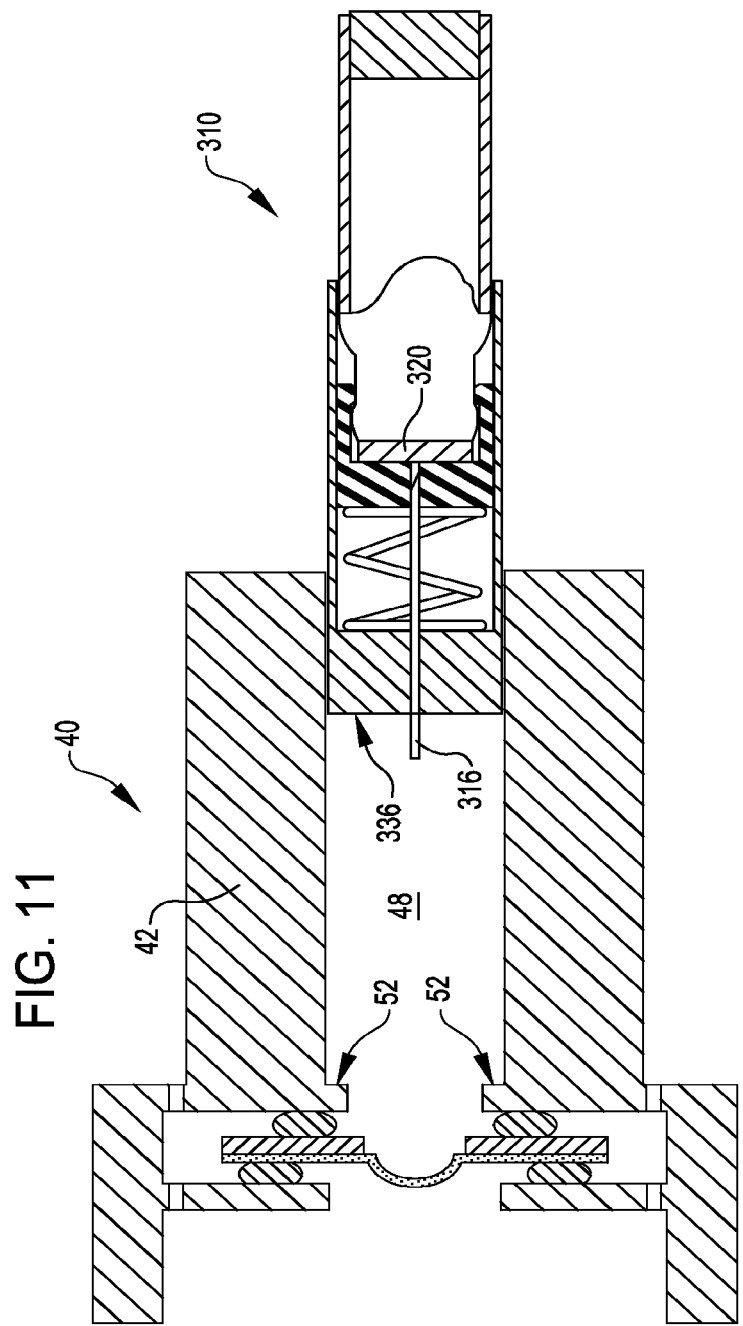
FIG. 11 is a side view illustrating the drug cartridge of FIG. 9 partially inserted into the inhaler of FIG. 2, in accordance with many embodiments.

FIG. 11 illustrates the self-puncturing liquid drug cartridge 310 partially inserted into the inhaler 40. As the self-puncturing liquid drug cartridge 310 is inserted into the receptacle 48, the self-puncturing liquid drug cartridge 310 remains in the first configuration in which the hollow needle 316 does not extend through the septum 320 until the exterior end wall surface 336 contacts the shelf 52.

Figure 12:
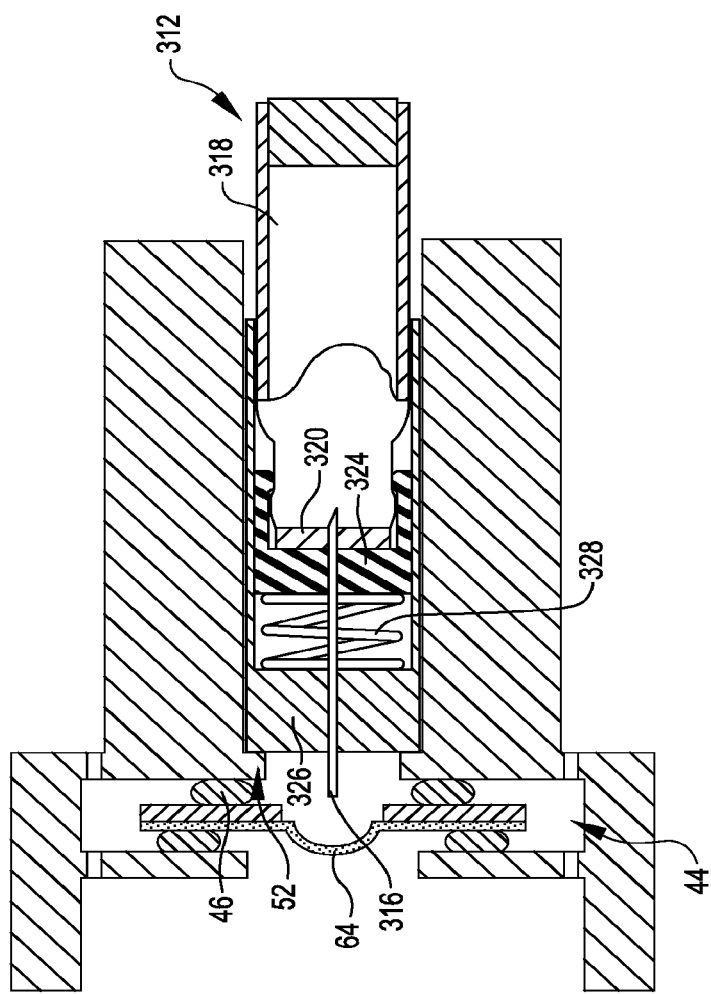
FIG. 12 is a side view illustrating the drug cartridge of FIG. 9 inserted into the inhaler of FIG. 2 to a depth sufficient to result in penetration of a hollow needle through a septum so as to establish a fluid path for ejection of liquid drug from the cartridge, in accordance with many embodiments.

FIG. 12 illustrates the self-puncturing liquid drug cartridge 310 almost fully inserted into the inhaler 40. In the illustrated configuration, the guide element 326 is in contact with the shelf 52 and the container assembly 312 has been pushed towards the guide element 326, thereby partially compressing the spring 328 and inserting the sharpened end of the hollow needle 316 through the septum 320. The force of the spring 328 holds the guide element 326 in contact with the shelf 52, thereby fixing the position of the ejecting end of the hollow needle 316 relative to the vibratable membrane 64 of the aerosol generator 44.

Figure 13:
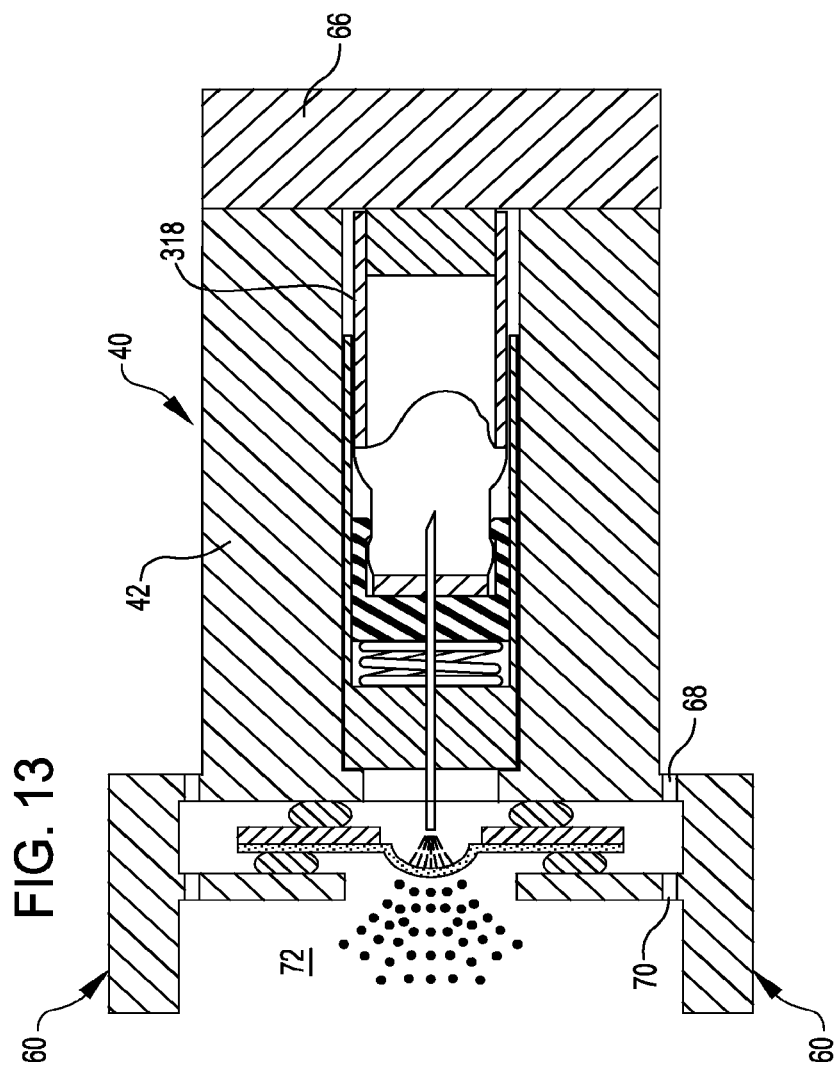
FIG. 13 is a side view illustrating the drug cartridge of FIG. 9 fully inserted into the inhaler of FIG. 2 and retained by an end member, as well as liquid drug ejected from the cartridge being aerosolized for inhalation by a user, in accordance with many embodiments.

FIG. 13 illustrates the self-puncturing liquid drug cartridge 310 fully inserted into the inhaler 40. An end member 66 retains the self-puncturing liquid drug cartridge 310 and reacts the force imparted to the container assembly 312 via the spring 328, which is in a compressed state. The spring 328 in a compressed state maintains the guide element 326 in contact with the shelf 52, thereby maintaining a preferred predetermined position of the ejecting end of the hollow needle 316 relative to the vibratable membrane 64. While the sharpened end of the hollow needle 316 is illustrated in FIG. 13 to be located a significant distance past the inner wall of the septum 320, in many embodiments the sharpened end of the hollow needle 316 is located closer to the septum 320 so as to increase the amount of insulin that can be dispensed from the cartridge.

The inhaler 40 can include a suitable actuator for displacing the piston 322 relative to the container 318 so as to eject a desired preselected dose of liquid drug from the container 318 via the ejecting end of the hollow needle 316. For example, the end member 66 and the housing 42 can form a pressurizable vessel into which air can be injected so as to displace the piston 322 towards the guide element 326. As another example, the piston 322 can be controllably displaced toward the guide element 326 via an actuation mechanism coupled with the end member 66 or acting through the end member 66.

In use, a user inhales from the mouthpiece 60 and the aerosol generator 44 simultaneously aerosolizes a dose of liquid drug ejected from the ejecting end of the hollow needle 316 via a corresponding actuation of the piston 322. The housing 42 includes one or more air inlets 68 and a restrictor array 70 by which air is introduced into a mixing chamber 72 for combination with the aerosolized dose of the liquid drug prior to inhalation by the user.

As another example, a self-puncturing liquid drug cartridge can be configured similar to the self-puncturing liquid drug cartridge 310 illustrated in FIG. 9, but without the spring 328. In such a configuration, the cartridge can be reconfigurable from a first configuration (similar to the first configuration of the self-puncturing liquid drug cartridge 310 illustrated in FIG. 9) in which the hollow needle 316 does not extend through the septum 320 and a second configuration (similar to the second configuration of the self-puncturing liquid drug cartridge 310 illustrated in FIG. 13) in which the hollow needle extends through the septum 320. For example, the cartridge can include one or more detent features (e.g., one or more interfacing features of the guide element 326 and the cap 324) that maintain the cartridge in the first configuration prior to installation into an inhaler. Upon installation of the cartridge into an inhaler, the one or more detent features can be configured to permit relative movement between the guide element 326 and the cap 324 in response to compression forces arising from the installation, thereby reconfiguring the cartridge into the second configuration. In many embodiments without the spring 328, the cartridge remains in the second configuration after being reconfigured into the second configuration. Additionally, one or more additional detent features (e.g., one or more interfacing features of the guide element 326 and the cap 324) that interface when the cartridge is in the second configuration can be used to maintain the guide element 326 in contact with the shelf 52, thereby maintaining a preferred predetermined position of the ejecting end of the hollow needle 316 relative to the vibratable membrane 64.

Figure 14:
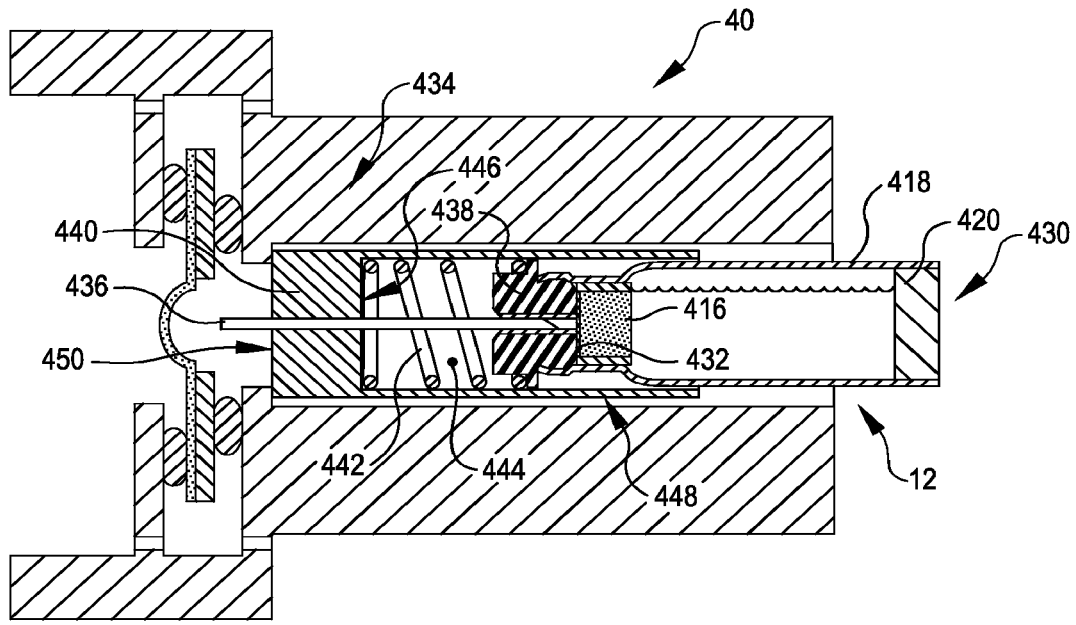
FIG. 14 is a side view of another self-puncturing liquid drug cartridge partially inserted into the inhaler of FIG. 2, in accordance with many embodiments.
Figure 15:
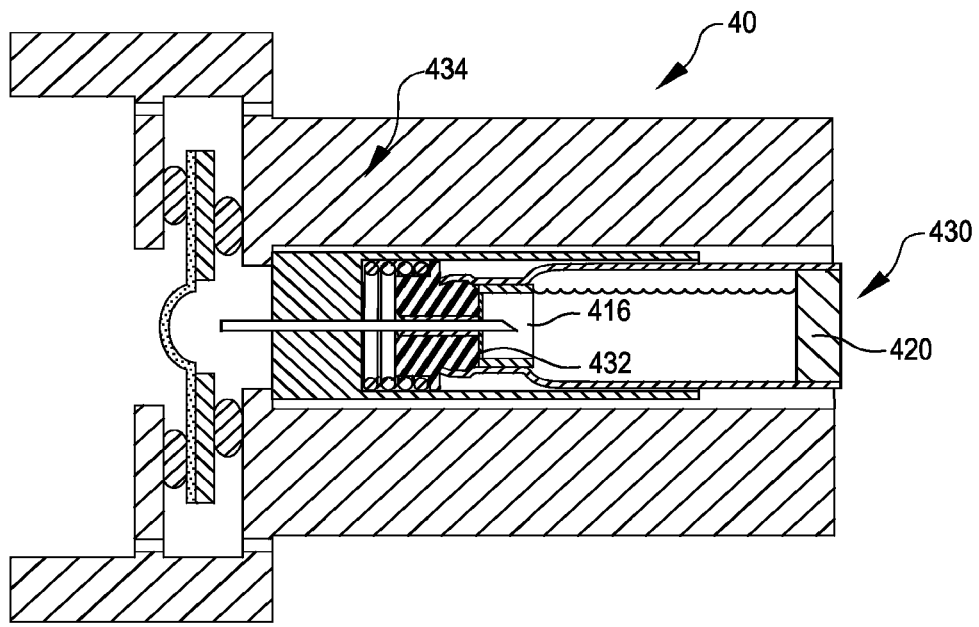
FIG. 15 is a side view illustrating the self-puncturing liquid drug cartridge of FIG. 14 inserted into the inhaler of FIG. 2 to a depth sufficient to result in penetration of a hollow needle through a septum and into a filter so as to establish a fluid path for ejection of liquid drug from the cartridge, in accordance with many embodiments.

FIGS. 14 and 15 illustrates a self-puncturing liquid drug cartridge 430 for use with the inhaler 40, in accordance with many embodiments. The self-puncturing liquid drug cartridge 430 includes a container assembly 412, a filter 416, a septum 432, and a needle assembly 434, which is coupled to the container assembly 412 and includes a hollow needle 436.

The container assembly 412 is configured to store a liquid drug for subsequent dispensing to an inhaler. The container assembly 412 includes a container 418 having openings at opposing ends of the container 418, the filter 416, the septum 432 sealing a first end of the container 418, and a piston 420 sealing a second end of the container 418. The septum 432 is configured to be punctured by the hollow needle 436 to establish a fluid path by which the liquid drug within the container 418 can be dispensed to an inhaler. The hollow needle 436 can penetrate partially into the filter 416 so that the liquid drug passes through at least a portion of the filter 416 before entering the hollow needle 436. The piston 420 is selectively slidable within the container 418 so as to eject a selected quantity of the liquid drug from the container 418 via the hollow needle 436.

The needle assembly 434 is reconfigurable between a first configuration (illustrated in FIG. 14) in which the hollow needle 436 does not extend through the septum 432 and a second configuration (see, e.g., FIG. 15) in which the hollow needle 436 extends through the septum 432. The needle assembly 434 includes the hollow needle 436, a cap 438, a guide element 440, and a spring 442. In the illustrated embodiment, the cap 438 is configured to couple the needle assembly 434 to the container assembly 412. Any suitable approach can be used to couple the needle assembly 434 with the container assembly 412. For example, in the illustrated embodiment, the cap 438 is configured to receive a first end portion of the container assembly 412 and retain the received portion via complementary snap fit features of the cap 438 and the container assembly 412. The guide element 440 includes a receptacle 444 configured to slidingly receive and interface with the cap 438 and a portion of the container assembly 412. Opposing ends of the spring 442 are coupled with an end wall 446 of the receptacle 444 and the cap 438, respectively. In the first configuration, the spring 442 is in an un-deflected configuration and maintains the illustrated separation between the cap 438 and the end wall 446 of the receptacle 444, thereby disposing the hollow needle 436 in the position illustrated relative to the septum 432. The guide element 440 has an exterior surface 448 and an exterior end wall surface 450.

FIG. 14 illustrates the self-puncturing liquid drug cartridge 430 partially inserted into the inhaler 40. As the self-puncturing liquid drug cartridge 430 is inserted into the receptacle 444, the self-puncturing liquid drug cartridge 430 remains in the first configuration in which the hollow needle 436 does not extend through the septum 432 until the exterior end wall surface 450 contacts the shelf 52.

FIG. 15 illustrates the self-puncturing liquid drug cartridge 430 fully inserted into the inhaler 40. In the illustrated configuration, the guide element 440 is in contact with the shelf 52 and the container assembly 412 has been pushed towards the guide element 440, thereby partially compressing the spring 442 and inserting the sharpened end of the hollow needle 436 through the septum 432. The force of the spring 442 holds the guide element 440 in contact with the shelf 52, thereby fixing the position of the ejecting end of the hollow needle 436 relative to the vibratable membrane 64 of the aerosol generator 44. An end member can be used to retain the self-puncturing liquid drug cartridge 430 within the inhaler and react the force imparted to the container assembly 412 via the spring 442, which is in a compressed state. The spring 442 in a compressed state maintains the guide element 440 in contact with the shelf 52, thereby maintaining a preferred predetermined position of the ejecting end of the hollow needle 436 relative to the vibratable membrane 64.

The inhaler 40 can include a suitable actuator for displacing the piston 420 relative to the container 418 so as to eject a desired preselected dose of liquid drug from the container 418 via the ejecting end of the hollow needle 436. For example, an end member and the housing 42 can form a pressurizable vessel into which air can be injected so as to displace the piston 420 towards the guide element 440. As another example, the piston 420 can be controllably displaced toward the guide element 440 via an actuation mechanism coupled with an end member or acting through the end member.

In use, a user inhales from the mouthpiece 60 and the aerosol generator 44 simultaneously aerosolizes a dose of liquid drug ejected from the ejecting end of the hollow needle 436 via a corresponding actuation of the piston 420. The housing 42 includes one or more air inlets 68 and a restrictor array 70 by which air is introduced into a mixing chamber 72 for combination with the aerosolized dose of the liquid drug prior to inhalation by the user.

The specification and drawings are, accordingly, to be regarded in an illustrative rather than a restrictive sense. It will, however, be evident that various modifications and changes may be made thereunto without departing from the broader spirit and scope of the disclosure as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the disclosure to the specific form or forms disclosed, but on the contrary, the intention is to cover all modifications, alternative constructions, and equivalents falling within the spirit and scope of the disclosure, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the disclosure and does not pose a limitation on the scope of the disclosure unless otherwise claimed. No language in the specification should be construed as indicating any non-claimed element as essential to the practice of the disclosure.

Disjunctive language such as the phrase "at least one of X, Y, or Z," unless specifically stated otherwise, is intended to be understood within the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Preferred embodiments of this disclosure are described herein, including the best mode known to the inventors for carrying out the disclosure. Variations of those preferred embodiments may become apparent to those of ordinary skill in the art upon reading the foregoing description. The inventors expect skilled artisans to employ such variations as appropriate and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A method of delivering an aerosolized medication to a user's respiratory system, comprising:
    detecting an inhalation by a user using an inhalation monitoring system;
    communicating a signal to a piston actuation system, the signal indicating that the inhalation has been detected;
    in response to receiving the signal, displacing, using the piston actuation system, a piston that is positioned at a distal end of a reservoir of a cartridge to force a volume of liquid medicament from the reservoir of the cartridge;
    filtering the volume of liquid medicament using a filter element positioned within an end cap of the cartridge that is positioned on a proximal end of the reservoir, the proximal end being on an opposite side of the reservoir as the distal end;
    ejecting the volume of liquid medicament onto a rear face of a mesh of an aerosol generator via an ejection opening of the end cap after the volume of liquid medicament has been filtered;
    vibrating the mesh of the aerosol generator to aerosolize the volume of liquid medicament to produce a plume of aerosolized medicament; and
    entraining the aerosolized medicament within inspiratory flow through a mouthpiece of an inhaler.

2. The method of delivering an aerosolized medication to a user's respiratory system of claim 1, further comprising:
    interfacing the cartridge with a housing of the inhaler prior to displacing the piston.

3. The method of delivering an aerosolized medication to a user's respiratory system of claim 1, further comprising:
    removing a removable cap from the end cap to expose the ejection opening, wherein the removable cap is configured to interface with the end cap such that the ejection opening is closed by the removable cap so as to block flow of the liquid medicament through the ejection opening any time the removable cap is coupled with the end cap.

4. The method of delivering an aerosolized medication to a user's respiratory system of claim 1, wherein:
the cartridge further comprises a check valve disposed between the end cap and the reservoir that is configured to permit only one-way flow in an outward direction from the reservoir to the ejection opening to block microbial ingress into the reservoir from the ejection opening.

5. The method of delivering an aerosolized medication to a user's respiratory system of claim 1, wherein:
the piston extends an entire distance between opposing sidewalls of the reservoir;
the piston is solid so as to prevent the liquid medicament from passing through and/or beyond the piston; and
the piston seals a distal end of the cartridge that is spaced apart from a proximal end of the cartridge.

6. The method of delivering an aerosolized medication to a user's respiratory system of claim 1, further comprising:
passing the inspiratory flow through a restrictor array prior to entraining the aerosolized medicament.

7. The method of delivering an aerosolized medication to a user's respiratory system of claim 1, wherein:
the filter element is configured to inhibit microbial ingress into the cartridge.

8. A method of delivering an aerosolized medication to a user's respiratory system, comprising:
detecting an inhalation by a user using an inhalation monitoring system;
communicating a signal to a piston actuation system, the signal indicating that the inhalation has been detected;
in response to receiving the signal, displacing, using the piston actuation system, a piston that is positioned at a distal end of a reservoir of a cartridge to force a volume of liquid medicament from the reservoir of the cartridge such that the volume of liquid medicament passes through a check valve that is configured to permit only one-way flow in an outward direction from the reservoir to block microbial ingress into the reservoir;
ejecting the volume of liquid medicament onto a rear face of a mesh of an aerosol generator via an ejection opening of an end cap after the volume of liquid medicament has passed through the check valve, wherein the end cap is positioned on a proximal end of the reservoir opposite the distal end;
vibrating the mesh of the aerosol generator to aerosolize the volume of liquid medicament to produce a plume of aerosolized medicament; and
entraining the aerosolized medicament within inspiratory flow through a mouthpiece of an inhaler.

9. The method of delivering an aerosolized medication to a user's respiratory system of claim 8, further comprising:
filtering the volume of liquid medicament using a filter element positioned within an end cap of the cartridge prior to ejecting the volume of liquid medicament.

10. The method of delivering an aerosolized medication to a user's respiratory system of claim 8, wherein:
the piston is air driven.

11. The method of delivering an aerosolized medication to a user's respiratory system of claim 8, further comprising:
sensing when a patient starts breathing; and
automatically activating the aerosol generator based on the sensed breathing.

12. The method of delivering an aerosolized medication to a user's respiratory system of claim 8, further comprising:
illuminating at least a portion of a chamber in which the liquid medicament is ejected using an ultraviolet light after entraining the aerosolized medicament within inspiratory flow to provide microbial control between doses.

13. The method of delivering an aerosolized medication to a user's respiratory system of claim 8, further comprising:
passing the inspiratory flow through a restrictor array prior to entraining the aerosolized medicament.

14. The method of delivering an aerosolized medication to a user's respiratory system of claim 13, wherein:
the restrictor array is configured to produce laminar flow that surrounds the aerosolized medicament.

15. A method of delivering an aerosolized medication to a user's respiratory system, comprising:
sensing an inhalation of a patient at a mouthpiece of an inhaler;
displacing a piston that is positioned at a distal end of a reservoir of a cartridge to force a volume of liquid medicament from the reservoir of the cartridge based on the sensed inhalation;
filtering the volume of liquid medicament using a filter element disposed within a neck of the cartridge;
introducing the filtered volume of liquid medicament into a proximal end of a conduit defined within an end cap that is coupled with the neck of the cartridge;
ejecting the volume of liquid medicament onto a rear face of a mesh of an aerosol generator via an ejection opening formed at a distal end of the conduit based on the sensed inhalation, wherein the end cap is positioned on a proximal end of the reservoir opposite the distal end;
vibrating the mesh of the aerosol generator to aerosolize the volume of liquid medicament to produce a plume of aerosolized medicament based on the sensed inhalation such that the volume of liquid medicament is aerosolized concurrently with the sensed inhalation; and
entraining the aerosolized medicament within inspiratory flow through the mouthpiece of the inhaler.

16. The method of delivering an aerosolized medication to a user's respiratory system of claim 15, further comprising:
sensing that the inhalation has stopped; and
pausing production of the aerosolized medicament based on sensing that the inhalation has stopped.

17. The method of delivering an aerosolized medication to a user's respiratory system of claim 15, wherein:
the cartridge further comprises a check valve disposed between the end cap and the reservoir that is configured to permit only one-way flow in an outward direction from the reservoir to the ejection opening to block microbial ingress into the reservoir from the ejection opening; and
the method further comprises filtering the volume of liquid medicament using a filter element positioned within an end cap of the cartridge prior to ejecting the volume of liquid medicament.

18. The method of delivering an aerosolized medication to a user's respiratory system of claim 17,
the filter element is positioned downstream of the check valve.

19. The method of delivering an aerosolized medication to a user's respiratory system of claim 15, further comprising:
priming the cartridge prior to ejecting the volume of the liquid medicament by displacing the piston until a drop of the liquid medicament is dispensed.

20. The method of delivering an aerosolized medication to a user's respiratory system of claim 19, further comprising:
  sensing, using aerosol generator software, that the mesh is wet; and
  stopping the priming based on the sensing that the mesh is wet.

* * * * *